United States Patent [19]

Ogren

[11] Patent Number: 4,817,044
[45] Date of Patent: Mar. 28, 1989

[54] COLLECTION AND REPORTING SYSTEM FOR MEDICAL APPLIANCES

[76] Inventor: David A. Ogren, 9965 Business Park Ave., San Diego, Calif. 92131

[21] Appl. No.: 56,070

[22] Filed: Jun. 1, 1987

[51] Int. Cl.$^4$ .................. G06F 15/42; G01D 9/00
[52] U.S. Cl. .................. 364/550; 340/825.06; 346/33 ME; 364/413.02; 364/479
[58] Field of Search .............. 364/200, 900, 143, 413, 364/415, 467, 479, 550; 346/33 ME; 340/825.06

[56] References Cited

U.S. PATENT DOCUMENTS

| | | | |
|---|---|---|---|
| 4,216,462 | 8/1980 | McGrath et al. | 364/415 |
| 4,359,632 | 9/1982 | Hansen et al. | 364/143 |
| 4,400,783 | 8/1983 | Locke, Jr. | 364/550 |
| 4,473,884 | 9/1984 | Behl | 364/479 |
| 4,546,436 | 10/1985 | Schneider et al. | 364/415 |
| 4,575,803 | 3/1986 | Moore | 364/550 |
| 4,612,620 | 9/1986 | Davis et al. | 364/550 |
| 4,658,371 | 4/1987 | Walsh et al. | 364/550 |
| 4,689,757 | 8/1987 | Downing et al. | 364/479 |
| 4,695,954 | 9/1987 | Rose et al. | 364/479 |

Primary Examiner—Parshotam S. Lall
Assistant Examiner—Kevin J. Teska
Attorney, Agent, or Firm—Charmasson & Holz

[57] ABSTRACT

A collection and reporting system for infusion appliance comprising a battery operated monitoring device connected to the power source of the infusion appliance which monitors its usage for a certain period of time, whereupon the data pertaining to the various assignments are transferred to collecting means and further listed by printing means. The data include information pertaining to the monitoring device itself, the infusion appliance being monitored, the patient data and the usage data indicative of the functioning status of the infusion appliance. Usage data are logged every six minutes. The data residing in monitoring device or the meter are collected, recorded, printed and then cleared every one hundred eighty-four days or whenever the storing capacity of the RAM of the meter is exceeded. An indicator is turned on at the six month point to signal the need for collecting data.

21 Claims, 4 Drawing Sheets

COLLECTION AND REPORTING SYSTEM FOR MEDICAL APPLIANCES

FIELD OF THE INVENTION

This invention relates to a monitoring system, and more particularly to a medical appliance monitoring apparatus, used in connection with a data collection system. More particularly, the invention relates to a medical appliance monitoring device attached to a medical appliance for logging the times that the appliance is on or off and storing the data pertaining to the instrument user, the instrument and monitoring device itself.

BACKGROUND OF THE INVENTION

New complex medical appliances are being increasingly used in hospital and home care milieus for sophisticated medical treatments. In particular, automatic, programmable infusion appliances for intravenous medication and enteral feeding have found wide use in the past two decades, concurrently with the development of integrated circuitry and microprocessors.

A patient to whom a medical appliance, such as an infusion pump, has been assigned is presently billed for the total time that the appliance was available to him, even though the appliance is intermittently used during its assignment to the patient (or to a location). Furthermore, a collection of data pertaining to the patient, to the medical appliance being used, and to the time that the appliance has been assigned to a patient, is still manually performed. That may imply delays in the billing procedures, is prone to transcribing errors and inequitably over or under states the rental fees.

Accurate and economical monitoring of the use of these appliances is also essential for maintenance and reliability purposes. Presently, medical appliances are serviced on the basis of the total time elapsed during assignments to particular patients rather than on the actual use of the appliances. More accurate monitoring of a medical appliance would allow determination of optimal maintenance, reduce the service costs and clearly assess the reliability of a particular medical appliance. Ideally, such monitoring should be entirely automatic and performed by computing means for developing data bases.

A monitoring device which would store the data related to the medical appliance and to the patient and which would automatically log clock times when the appliance is on or off during a particular usage situation is not known to exist.

It is then an object of the present invention to provide a monitoring device which is capable of logging the clock times that a medical appliance is on or off during a particular usage situation.

It is another object of the present invention to provide a fully automated transfer of data from the monitor to the data collecting means.

It is still another object of the present invention to provide an accurate, economical and noninvasive monitoring device for medical appliances that optimizes maintenance routines, precisely assesses reliability properties of the medical appliance, verifies utilization periods for compliance with medical orders and medical/legal substantiation and ensures equitable rental billings based on the actual usage of the medical appliance.

SUMMARY OF THE INVENTION

The above and other objects of the present invention are accomplished by providing a battery operated device which monitors to the power source of an electric instrument and determines its usage for a certain period of time, whereupon the data pertaining to the various assignments are transferred to collecting means and further listed by printing means. These data include information which identifies the monitoring device, the electrical instrument being monitored, the patient, and the functional status of the instrument instrument over time. Usage data are logged every six minutes. The data residing in the monitoring device or the meter are collected, recorded, printed and then cleared as needed or up to every one hundred eighty-four days or whenever the storing capacity of the random access memory (RAM) of the meter is exceeded. An indicator is turned on at the six month point to signal the need for collecting data. The above and other objects, advantages and features of the present invention will become more readily apparent from a review of the following specifications when taken in conjunction with the drawings.

DESCRIPTION OF THE PREFERRED EMBODIMENTS OF THE INVENTION

Figure 1:
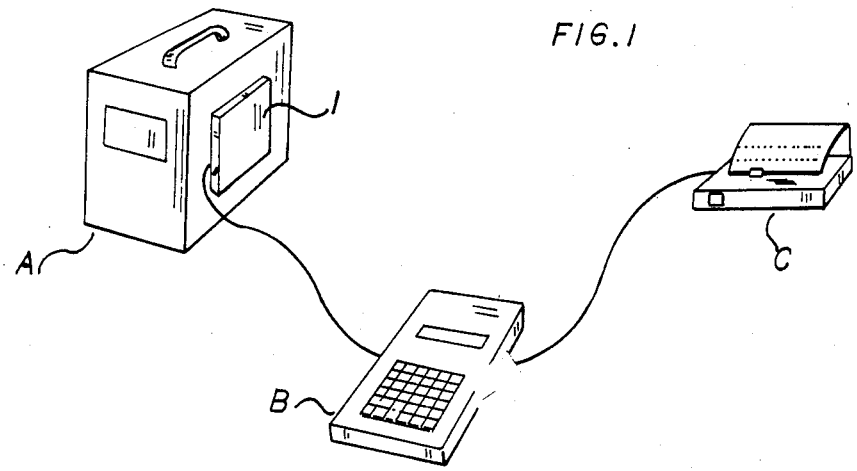
FIG. 1 schematically represents the entire monitoring system.

Referring to the drawing, FIG. 1 depicts the d embodiment of the monitoring system. The system of the present invention consists of a usage monitoring device 1("hereinafter called the meter"), attached to the host instrument A (hereinafter called the "instrument"), a desk-top or portable battery operated data collector unit B to service the meters (hereinafter called the "collector") and a table mounted electromechanical printer C (hereinafter called the "printer") to print house-keeping and usage data from the meter.

The instrument A represented on FIG. 1 is a medical appliance for illustrative purposes but could be replaced by any other medical, commercial or industrial device which needs to be monitored.

The meter 1 has typically the form of a parallelipipedic enclosure and can be easily installed on one side of the medical appliance A. It has the typical following dimension: 4" (width); 5.5" (length); 1.2" (depth). Its overall weight would not exceed approximately two pounds. Preferably the housing of the device would be constructed of high impact polymer. If made of metal, the meter's surface is passivated according to known methods.

The meter is attached to the medical appliance A in the monitoring system of the present invention. The data pertaining to the usage of the medical appliance are acquired by the meter at regular intervals. The time resolution selected in the system of the present invention is six minutes, thus, no detected operation of the instrument is logged as less than six minutes (that time base implies 240 data transfers per day).

The meter 1 is provided with a battery which allows it to function for a period of approximately 6½ months (preferably of at least 194 days). The data storage medium of the meter is also capable of storing the usage data of instruments for that same period of time.

The meter 1 is equipped with an overflow device designed to indicate that the functioning period has elapsed or that portion of the RAM devoted to store the patient data has no remaining capacity for an additional set of patient data. Preferably, the period of time which would trigger the meter overflow is 184 days. The meter keeps track of the days elapsed by means of a counter which registers each data transfer. When 184×240 data transfers have been counted and registered, a triggering signal is sent by the meter counter to an electromechanical indicator provided in the meter, as described herebelow.

This electromechanical detector is hence set and indicates that the data need be collected by the collector. The electromechanical indicator does not consume power except when being set or reset. In the present invention, the indicator is labeled "service meter".

The data can be partitioned in two categories, they must indicate both the attachment of the meter to the host instrument, and the assignment of the instrument to the patient.

The data indicating the attachment of the meter to the instrument, hereinafter the instrument data, consists of the military time (based on 24 hours instead of 12 hours per day), day, month an year that the meter was initialized. They also include the model number of the instrument, the instrument serial number, the meter's serial number and the name of the owner of the instrument and of the meter.

The data pertaining to the patient, hereinafter the patient data consists of an eight character alphanumeric patient identification code, the patient's name and the military time, day, month and year that the instrument was assigned to the patient.

The data need be transferred in both directions between the meter and the collector, when data collection occurs. The collector is appropriately programmed to prompt and realize the data transfer and to display appropriate data for the collector agent at the collector. Preferably, the data transfer rate between the meter and the collector amounts approximately to 9600 baud, which allows transfer of thirty days of usage data plus housekeeping data in fifteen seconds or less.

The printer C is connected to the collector B and is capable of listing housekeeping and usage data on hardcopy. The collector and the printer are advantageously selected to allow the transfer and the listing of usage and housekeeping data from at least fifty appliances, each of which contains up to six months of usage data, in an overall time of one hour or less.

The following table illustrates a printout typically produced by the combination of a meter/collector/printer:

TABLE

| | | | |
|---|---|---|---|
| Asset Owner: | Omed Systems, Inc. | | |
| | 9965 Business Park Avenue, Suite A | | |
| | San Diego, California 92131 | | |
| Instrument Model: | Instrument: Sigma 6000 | | |
| Instrument Serial: | Serial: 3498313456 | | |
| Meter Serial Number: | Meter Serial: 17025 | | |
| Patient Data: | Patient: | B2CDE6FG John Doestoevski 1154 16 Dec 86 | |
| Usage Data: | Date | On | Off |
| | 16 Dec | 1206 | 1324 |

TABLE-continued

| | | | | |
|---|---|---|---|---|
| | 16 Dec | 2212 | ... | |
| | 17 Dec | ... | 0530 | |
| Patient Data: | Patient: | unassigned 1436 18 dec 86 | | |
| Usage Data: | 19 Dec | 1536 | 2212 | |
| | 31 Dec | 2318 | ... | |
| Total Assigned Monthly Hours used: | | December assigned hours: | | 8.6 |
| Total Unassigned Monthly Hours used: | | December unassigned hours: | | 7.3 |
| Total Days During Month with at least one use: | | December usage days: 4 | | |
| Same Data for Next Month: | Patient: | unassigned 1436 18 Dec 86 | | |
| | Date | On | Off | |
| | 2 Jan 87 | ... | 0912 | |
| | Patient: | Silvia Green 1242 4 Jan 86 | | |
| | 4 Jan 87 | 1248 | ... | |
| | 8 Jan 87 | ... | 1018 | |
| | Patient: | unassigned 1318 8 Jan 86 | | |
| | January assigned hours: | 93.5 | | |
| | January unassigned hours: | 33.2 | | |
| | January usage days: | 7 | | |

The printout is formatted as follows: The instrument data are listed first and referred to the initialization phase of the attachment of the meter to the instrument. The owner of the meter or of the instrument/meter combination is the sole person to have the ability to initialize the meter or modify the instrument data. The owner is referred to as "asset owner" in the formatted printout. The instrument user is excluded from having access to the instrument data by state-of-the-art software or operating modes.

Below the instrument are printed patient data and for each patient, the usage data relating to that patient. The usage data indicate the times when the instrument was turned on and turned off. As mentioned hereabove, the time resolution of the intervals is six minutes. Patient and usage data can be added to the listing when the instrument is assigned to a new patient. Reassignment of the meter to a new patient should indeed not cause current or previous patient data to be lost from the meter 1. Erasure of any usage or patient data only occurs when the asset owner reinitializes the meter after the data stored in the meter has been collected and recorded. Under no circumstances while battery is charged can the usage data be erased, altered or entered by either the asset owner or the user before the data collection. As the instrument can be assigned to an anonymous user or simply not assigned to a patient at all, the patient data need not be entered with the exception of the date and time. As noted hereabove, the reassignment of the instrument to an anonymous user does not affect the data previously stored.

After all the data have been collected the meter is reinitialized by the asset owner, which implies the clearing of the housekeeping and usage data previously stored.

The collector B has sufficient software to enable the operator to determine if a given patient or patient identification code is resident in the collector memory and to print the housekeeping and usage data for this single patient in the aforementioned printer format. It is also desirable that the printout contain the total elapsed time and duty cycle, that is, the percentage of total time the appliance is on, for each usage situation, as illustrated on FIG. 2.

Figure 2:
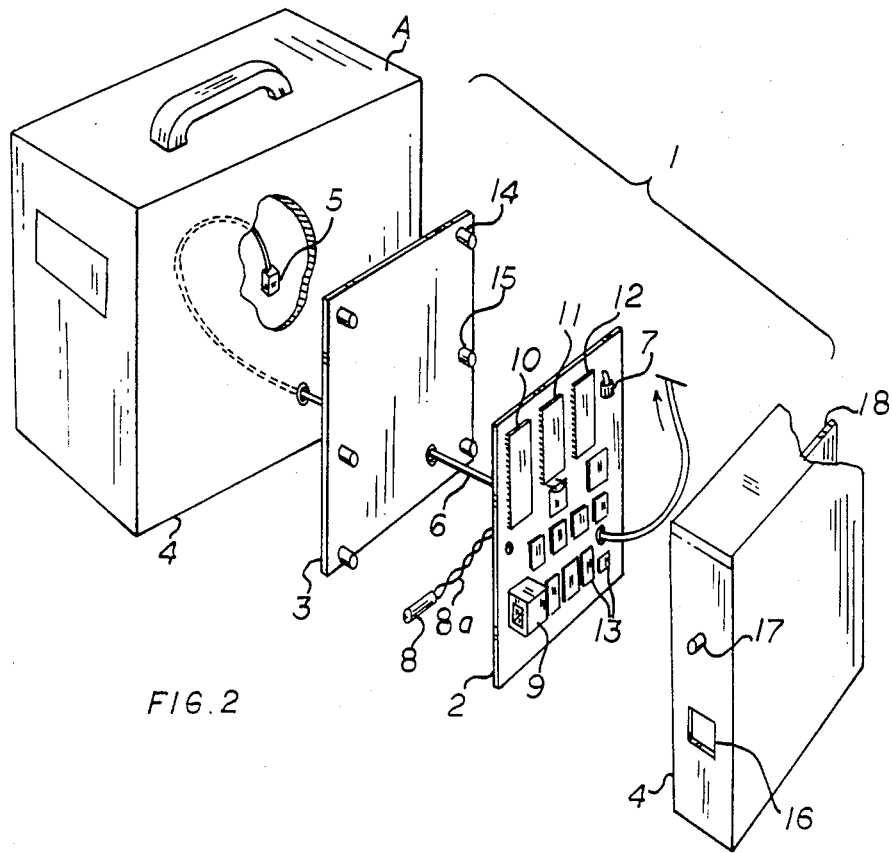
FIG. 2 is an exploded view of the monitoring device.

Referring now to FIG. 2, there is illustrated an implementation of a meter 1 in accordance with the invention in an exploded view. The meter 1 is attached to a medical appliance A by means of a mounting plate 3 on one side of the appliance A. The meter itself consists of a cover 4, of a printed circuit board 2 and of the aforementioned mounting plate 3. Six captive nuts 14 secure the mounting plate 3 to the appliance A. Six male friction fasteners 15 attached to the mounting plate 3, pass through the circuit board 2 and engage wiping holes (not shown) in bosses which are integral with a cover 4 on the inside.

The medical appliance A comprises an on-off detector 5 on the side to which the meter 1 is attached. This detector 5 is connected to the circuit board 2 by means of a fiber optic cable 6, which threads through protective grommets in the mounting plate 3 and circuit board 2. The cable then bends and terminates at the receiver connector 7. The cable 6 can also advantageously be a coaxial cable.

The circuit board 2 comprises an 8-bit multiport microprocessor 10, a programmable read-only memory (PROM) 11, a random access memory (RAM) 12, and integrated circuits for an accurate internal time base 13. All integrated circuits are preferably CMOS (complementary metallic oxide semiconductor) implementations in order to achieve low power consumption.

The meter 1 further includes an electromechanical flag indicator 8, for indicating meter overflow. The indicator 8 is attached by a twisted wire pair 8a to the circuit board 2 and connected to the microprocessor 10. When assembled, the flag indicator 8 lodges in a snap-in cover lens 17 provided on the cover 1. Advantageously, the indicator 8 can be a thermal flag indicator.

The flag indicator 8 is flashed at the six month point to indicate the need for preventive maintenance. During that operation by the collecting agent, the data are collected, recorded whereas the meter is reinitialized.

The data transfer is performed by means of a serial port connector 9, which has the same appearance as an 8-pin phone jack. An opening 16 is provided on one side of the cover 4 and allows the serial port connector 9 to protrude. The phone jack is hence easily accessible through the cut-out. A separate interconnect modulator is provided between the meter and the collector in the form of an 8-pin telephone-type cable including an interface box for adjusting handshake voltages.

Figure 3:
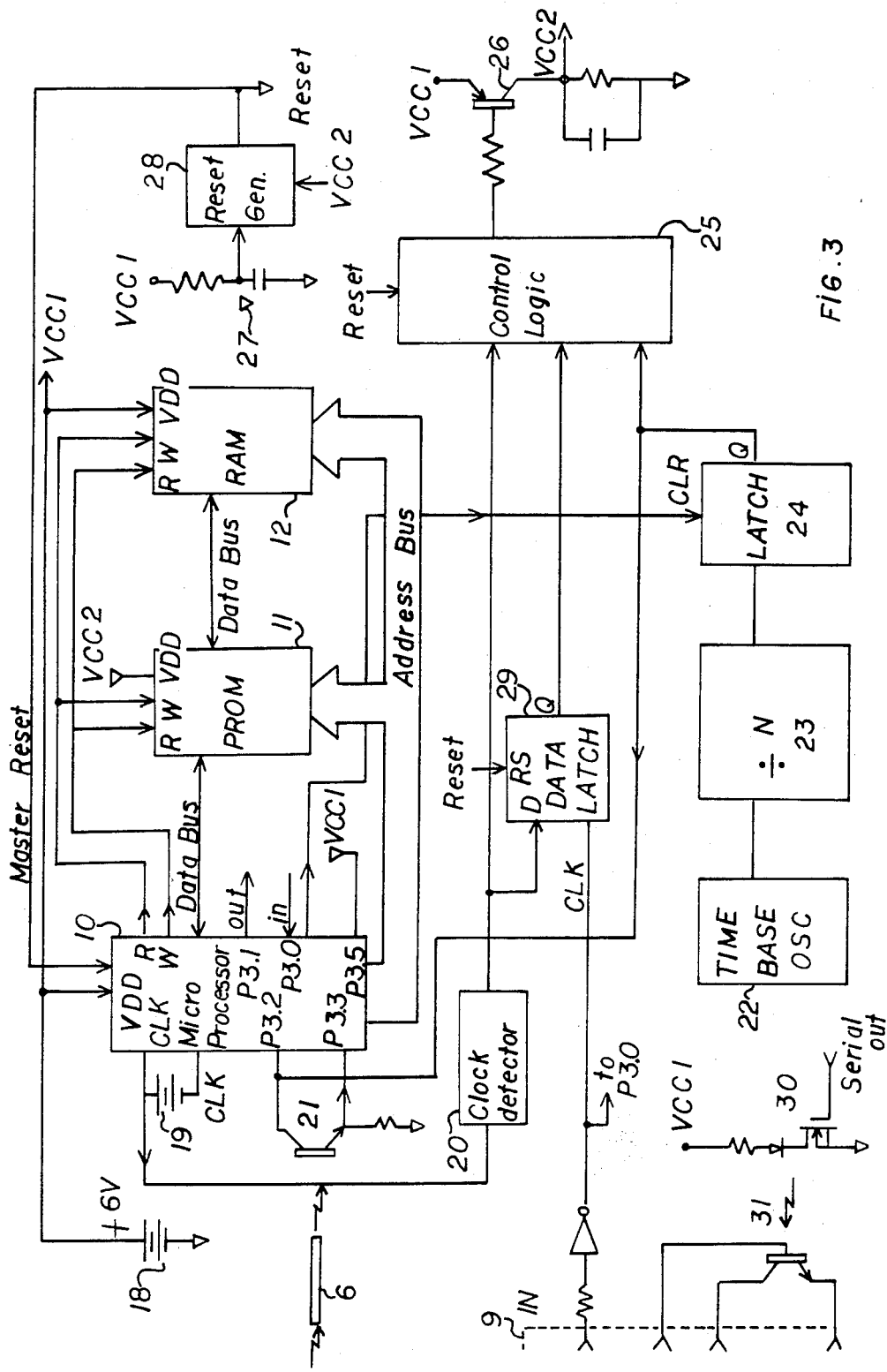
FIG. 3 is a block diagram illustrating the circuitry block of FIG. 2 in more detail.

With reference to FIG. 3, there is illustrated in block diagram the monitoring device described in FIG. 2. The flow charts showing the sequence of operations performed by the processing means described on FIG. 3 is represented on FIGS. 4A and 4B.

The microprocessor 10, the RAM 12 and the PROM 11 share a common 8-bit data bus as well as an 8-bit address bus. The microprocessor 10 can be set in different modes. One of them is the "power down" mode whereby the microprocessor 10 is able to lock static data onto those of its ports enabled as outputs and to terminate its internal data processing functions.

The microprocessor 10 is also able to shut off its internal clock oscillator driven by the attached quartz crystal 19. The microprocessor 10 remains in this state until it receives a master interrupt at which time it resets its clock and commences program execution as directed by the program stored in the PROM 11.

The microprocessor 10 has typically four bi-directional I/O ports. In one preferred embodiment of the present invention, one port is connected to the data bus, two other ports are connected to the address bus and the fourth port is used for miscellaneous input/output functions.

The supply rail VCC1 is provided by a lithium flat pack battery 18 mounted against the cover 4 of approximately 1.5 ampere hours of energy storage. Both the RAM 12 and the microprocessor 10 are permanently powered by the battery 18. In order to minimize the battery when the processor is powered down, a bipolar switch 26 controls the supply access to the PROM 11. The battery 18 is designed to furnish adequate power for the six months period which elapses between two data collections.

Figure 4A:
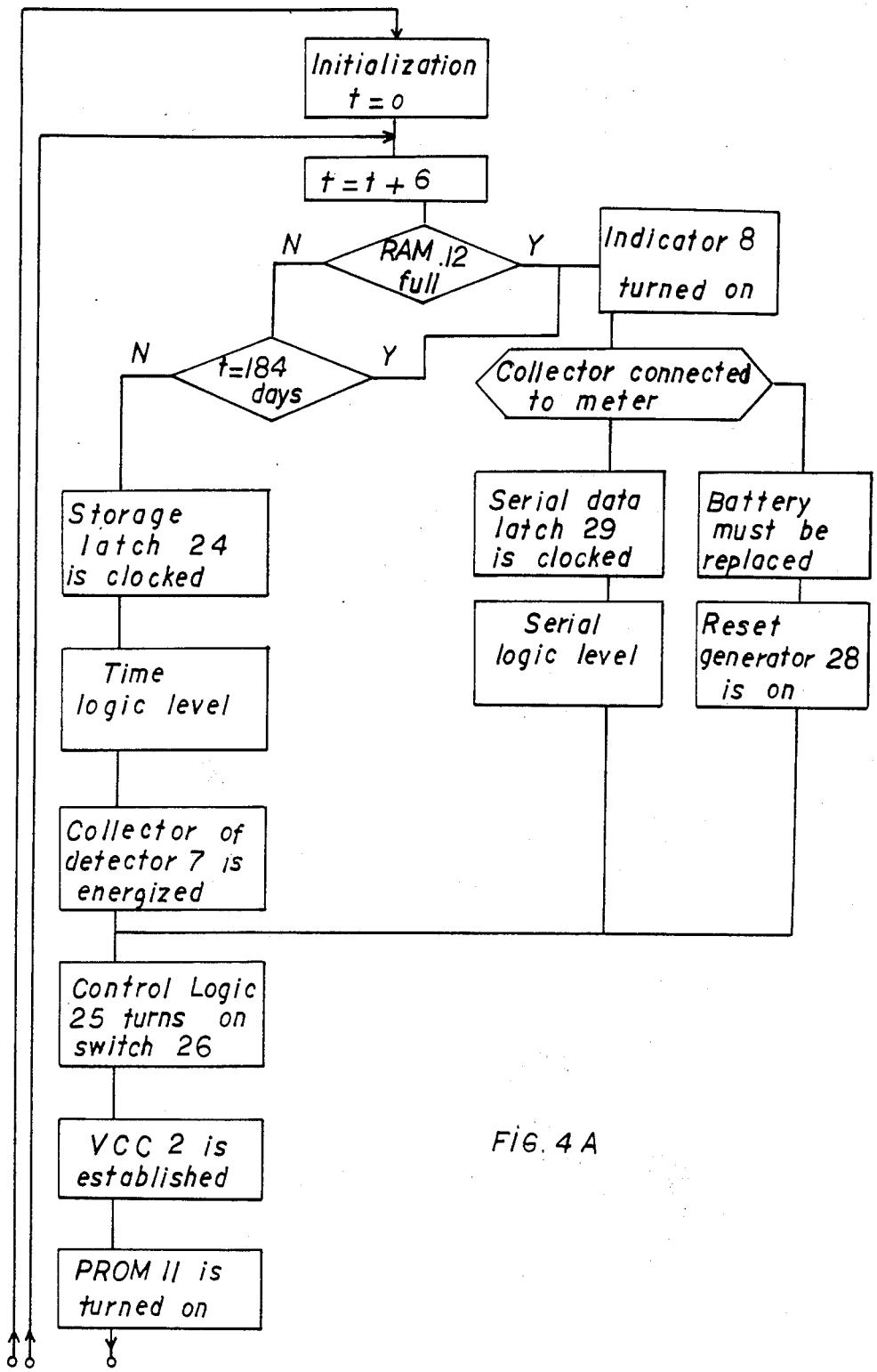
FIGS. 4A and 4B are flow-charts illustrating the sequence of operations performed by the microprocessor.
Figure 4B:
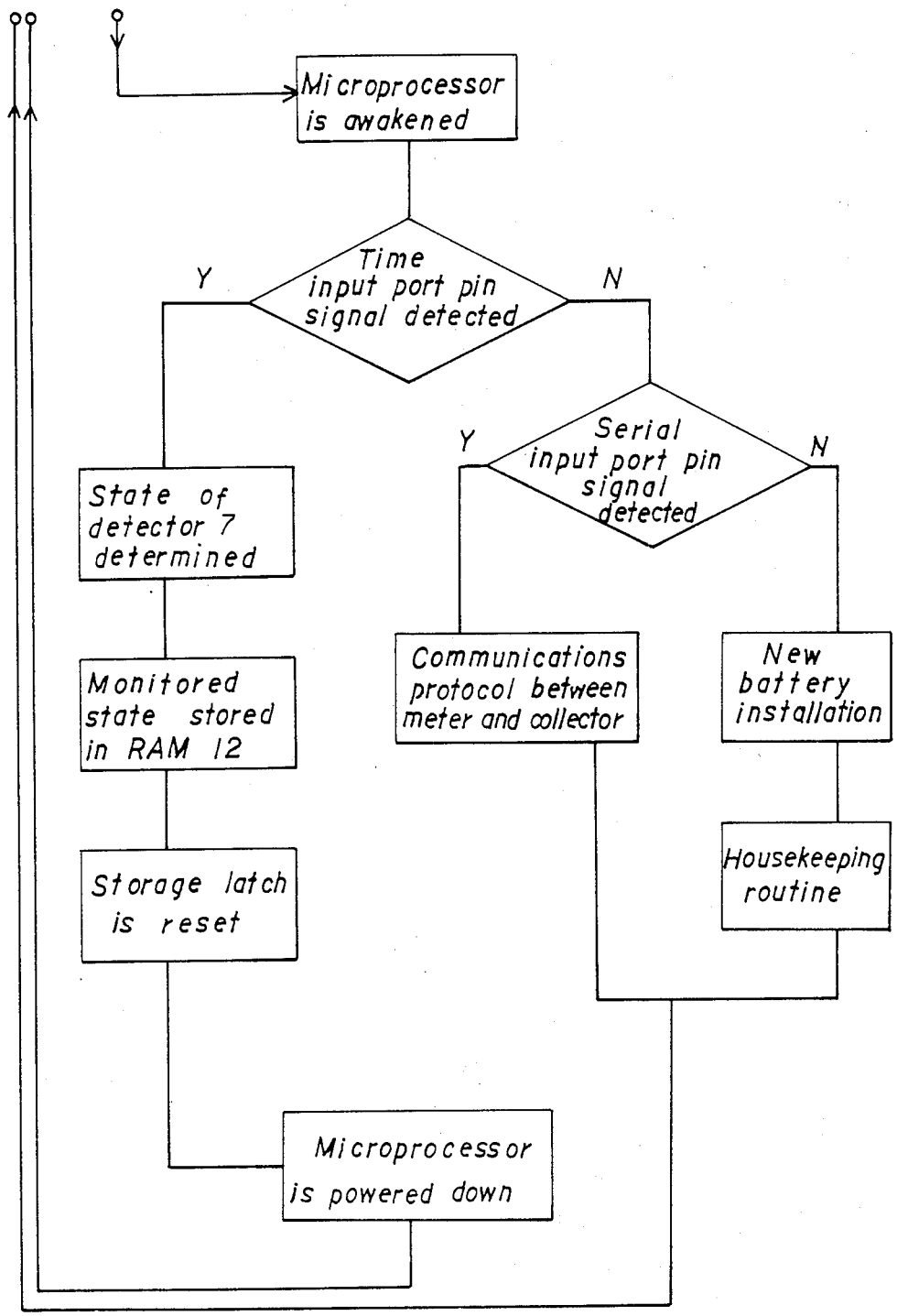

As shown in FIGS. 4A and 4B, the microprocessor 10 can be set in three modes of operations. In the first mode of operation, the microprocessor 10, initially powered down, is awakened by a time signal occurring every six minutes. More specifically, a precision time base oscillator 22 generates a square wave which is divided down by a multistage ripple counter 23 to produce a square wave with a period of six minutes. The rising edge of this waveform clocks the storage latch 24 which sets the Q output producing the TIME logic level. The TIME logic level energizes the collector of the infrared detector 21 in the receiving connector 7, which may or may not be enabled for conduction by infrared energy entering on fiber optic cable 6, depending on the state of the appliance being monitored. The TIME logic level inputs to the control logic 25 which turns on the switch 26 and establishes the supply rail VCC2 to the PROM 11 before the microprocessor 10 is awakened. The rising edge of VCC2 causes the reset generator 28 to output a master reset to the microprocessor 10, thereby waking it up. The microprocessor 10 determines that it has been awakened by the TIME logic level by looking at input port pin P3.2. It then looks at a state of detector by monitoring input P3.3. A monitored state is processed and stored at a single bit value of 0 (appliance off) or 1 (appliance on) in the RAM 12. The microprocessor 10 then resets the storage latch 24 and reenters its "power down" state. In this way a string of appliance status bits can be built up at six minute intervals at sequential address bits in the RAM 12, over a period of six months.

Two other modes of operation of the microprocessor 10 are also possible.

In the second mode of operation, the microprocessor 10 is awakened by a signal indicating that the data are to be transferred to the collector. Serial data are entered from the collector, typically a portable computer, through the "serial data in" pin on the data communications connector 9. The first rising edge of this data clocks the serial data latch 29, producing a high output on Q, which in turn stimulates the control logic 25 to turn on VCC2 again. In the same manner as described hereinabove, the rising edge of VCC2 initiates a processor reset. The microprocessor 10 determines that the wake up was occasioned by a serial data input by monitoring "serial data in" on pin P3.0 and finding a data stream. The microprocessor 10 then enters a data communications mode and carries out a bi-directional protocol on the pin P3.0 SERIAL IN, and P3.1 SERIAL OUT, with the collector. This protocol exchanges instrument data, patient data and usage data between the collector and the RAM 12.

The microprocessor 10 can also be set in a third mode when a new battery is to be installed after a six month period or preferably a greater lapse of time. The installation of a new battery supplying the rails VCC1 and VCC2 (not shown) causes the RC time delay 27 to send a temporary low level to the reset generator 28 because the capacitor in RC time delay 27 is discharged. Consequently, the reset generator 28 generates the microprocessor reset. When the microprocessor 10 has been reset, it monitors first the input port pin P3.2 for a TIME logic level. If that operation produces a negative result, it then monitors the serial date of port P3.0. Finding that neither of those ports is responsible for the "wake up", the microprocessor 10 infers that, by default, the reset was generated by a new battery 18 installation. The processor software then executes a special housekeeping routine to set up the memory space and the processor's internal structures. Data logging and data communications are temporarily stopped and can be resumed after the new battery is installed. The replacement of the battery 18 is performed such that it does not affect the data previously stored in the RAM 12.

In all three modes of operations, a clock detector circuit 20 is capable of determining if the microprocessor 10 is on or off by monitoring the microprocessor crystal 19. When the microprocessor 10 is being reset by one of the signals indicative of the operation mode the microprocessor crystal 19 generates a high level, CLOCK ON, which is sent as an input signal to the control logic 25. That ensures that the supply of rail VCC2 remains on as long as the processor is functioning, irrespective of the housekeeping resets that are applied to the serial data latch 29, and the time storage latch, 24. 5 Serial data are outputted from the meter by means of a MOSFET transistor 30 and optical coupler 31. The coupler 31 protects the meter from spurious static electricity discharges that can occur between the collector 2 and the meter 1, when the data plug is inserted into the jack 9. Such an operation is performed by breaking any complete circuit for the static electricity that could otherwise exist between SERIAL DATA IN—SERIAL OUT. With reference to FIGS. 4A and 4B again, there is illustrated a flow chart indicative of the three modes of operation hereabove described. It should be noted that other modes of operation can be added to the basic set of operations performed by the preferred embodiment of the present invention.

While the invention herein disclosed has been described by means of a specific embodiment and one application thereof, there are numerous modifications and variations thereof which could be made by those skilled in the art. It is therefore to be understood that within the scope of the appended claims, the invention may be practiced otherwise than as specifically described herein.

What is claimed is:

1. In combination with an electric consuming medical appliance device or patient monitoring device, a usage monitoring device for acquiring usage data solely from input electrical means to said electrical device, said usage monitoring device comprising:
   logging means for acquiring usage data from said input electrical means wherein said usage data are representative of at least two states indicative respectively of the functioning or the nonfunctioning of said input electrical means;
   storing means mounted within said logging means for accumulating said usage data during a first mode of operation; and
   means for retrieving said data from said storing means during a second mode of operation.

2. The combination of claim 1, wherein said logging means comprise:
   means for generating a first periodic a signal; and
   means responsive to said signal for setting said first mode of operation for loading said data at regular first periodic intervals.

3. The combination of claim 2, wherein said means for setting said first mode of operation comprises:
   a first input port connected to said means for generating; and
   means for initiating said logging means upon detection of said first periodic signal signal on said first port.

4. The combination of claim 1, which further comprises a programmable data microprocessor including said logging means, said means for setting and said means for triggering, where said microprocessor is directly attached to said medical device.

5. The combination of claim 4, wherein said microprocessor further comprises a separate power supply and means for a third mode of operation allowing replacement of said separate power supply after retrieval of usage data.

6. The combination of claim 5, wherein said means for a third mode of operation is responsive to said means for interpreting.

7. The combination of claim 1, wherein said means for retrieving said usage data comprises:
   means for issuing a second periodic signal;
   means responsive to said second periodic signal for triggering said second mode of operation for retrieving said stored usage data at regular second time intervals.

8. The combination of claim 1, wherein said means for triggering said second mode comprise;
   a second input port connected to said means for issuing; and
   means for interpreting said first and second periodic signals on said first and second ports.

9. The combination of claim 7, further comprising separate means for visually indicating that said second time interval has elapsed.

10. The combination of claim 9, which comprises means for energizing said indicating means when said storing means have no remaining capacity, said second time interval having not elapsed yet.

11. The combination of claim 9, wherein said indicating means comprise at least one electromechanical flag indicator.

12. The combination of claim 9, wherein said indicating means comprise at least one thermal flag indicator.

13. The combination of claim 7, wherein said second time intervals are set commensurately with the capacity of said storing means and the rated lifetime of said separate power supply.

14. The combination of claim 13, wherein said logging means comprise at least one programmable read-only memory and said storing means comprise at least one random-access memory.

15. The combination of claim 13, wherein said storing means also include information pertaining to a user of said medical device, and means for entering said information into said storing means before said medical device is assigned to said user.

16. The combination of claim 13, wherein said storing means also include information pertaining to said input electrical means and said logging means, said information being recorded before said input electrical means are put into use.

17. The combination of claim 13, which comprises means for clearing said storing means after said data has been retrieved.

18. The combination of claim 13 which comprises at least one fiber optic cable connecting said logging means to said input electric means.

19. The combination of claim 13 which comprises at least one coaxial cable connecting said logging means to said input electrical means.

20. The combination of claim 13, further comprising means for recording data other than said usage data connected to said retrieving means.

21. The combination of claim 20, wherein said recording means comprise at least one printer.

* * * * *